(12) United States Patent
Ouchi

(10) Patent No.: US 7,468,034 B2
(45) Date of Patent: Dec. 23, 2008

(54) BIOLOGICAL INFORMATION MONITORING APPARATUS

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 362 days.

(21) Appl. No.: 10/555,873

(22) PCT Filed: Mar. 23, 2005

(86) PCT No.: PCT/JP2005/005998

§ 371 (c)(1),
(2), (4) Date: Nov. 7, 2005

(87) PCT Pub. No.: WO2005/092190

PCT Pub. Date: Oct. 6, 2005

(65) Prior Publication Data

US 2006/0217612 A1 Sep. 28, 2006

(30) Foreign Application Priority Data

Mar. 26, 2004 (JP) .............................. 2004-092401

(51) Int. Cl.
*A61B 5/02* (2006.01)
*A61B 5/00* (2006.01)
(52) U.S. Cl. ...................................... 600/481; 600/300
(58) Field of Classification Search ......... 600/300–301, 600/407, 483, 485, 500–504, 529–543
See application file for complete search history.

(56) References Cited

U.S. PATENT DOCUMENTS

| 4,958,638 | A | 9/1990 | Sharpe et al. ............ 128/653 R |
| 5,766,208 | A | 6/1998 | McEwan .................... 600/595 |
| 2003/0149346 | A1* | 8/2003 | Arnone et al. .............. 600/309 |
| 2004/0058339 | A1 | 3/2004 | Nagel et al. .................... 435/6 |
| 2004/0210155 | A1* | 10/2004 | Takemura et al. ........... 600/534 |

FOREIGN PATENT DOCUMENTS

| EP | 1 400 800 A2 | 3/2004 |
| GB | 2 349 759 A | 11/2000 |
| JP | 10-229973 | 9/1998 |
| JP | 2002-576 | 1/2002 |

\* cited by examiner

*Primary Examiner*—Charles A Marmor, II
*Assistant Examiner*—Christian Y Jang
(74) *Attorney, Agent, or Firm*—Fitzpatrick, Cella, Harper & Scinto

(57) ABSTRACT

A biological information monitoring apparatus highly precisely observes a clothed subject who is taking any desired posture. The apparatus acquires information on positional displacements of the surface of a living body, by generating a high-frequency electromagnetic wave to radiate it into air, detecting the electromagnetic wave scattered by the surface of the living body, computationally determining the changes with time of the positional displacements of the surface of the living body from the state of propagation of said electromagnetic wave and computationally determining characteristic quantities of vibrations of the living body such as the pulse or the respiration from the changes with time as biological information.

6 Claims, 6 Drawing Sheets

BIOLOGICAL INFORMATION MONITORING APPARATUS

TECHNICAL FIELD

This invention relates to a biological information monitoring apparatus for acquiring biological information including the respiratory condition, the pulse wave, the pulse rate and so on of a living body, or subject, judging the psychosomatic condition of the subject and taking out the judgment as output signal in order to grasp the physical and emotional conditions and support the daily life of the subject.

BACKGROUND ART

Known apparatus for monitoring the respiratory condition, the pulse rate and so on of a living body, or subject, include those comprising one or more than one sensors to be put on the body of the subject or those adapted to observe the subject while the subject is lying still in bed. Japanese Patent Application Laid-Open No. 2002-576 discloses an apparatus comprising one or more than one contact type electrodes to be put on some of the finger tips and/or either or both of the ear lobes and/or irradiating a beam of light onto the body of the subject in order to detect necessary information. The disclosed apparatus has advantages including that it is resistant against external noises and that the components of the apparatus to be put on the subject are lightweight and compact.

On the other hand, Japanese Patent Application Laid-Open No. H10-229973 discloses an apparatus comprising one or more than one vibration detection means to be arranged in a bed or a chair in order to detect fine vibrations of the body of the subject caused by the circulation of blood of the subject who is lying on the bed or sitting on the chair, whichever appropriate, for the purpose of monitoring the biological information of the subject. FIG. 9 of the accompanying drawings schematically illustrates the disclosed apparatus. A supersonic sensor or an infrared sensor 111, which is a non-contact type sensor, can be used as vibration detection means for detecting the displacement M of the subject 112 shown in FIG. 9. A piezoelectric sensor may be used to monitor the vibrations of the body when the subject is lying on the bed. The detected vibrations of the body may be displayed on a display 113 that is buried in the head wall 110 as shown in FIG. 9.

While monitoring apparatus of the type having components to be put on the body of the subject can be handled with ease and light weight, they are neither convenient nor comfortable when used in daily lives. On the other hand, monitoring apparatus comprising components arranged in a bed or a chair are also rather inconvenient because the subject is forced to quietly keep a predetermined posture in the bed or on the chair for the purpose of monitoring. When ultrasonic waves or infrared rays are used for non-contact sensors, the subject can voluntarily take a posture that is comfortable to him or her because biological information can be acquired remotely. However, the wear and the hair of the subject reflect and absorb ultrasonic waves and infrared rays to operate as obstacles so that only limited sites can be observed by such means if the subject is clothed. Additionally, movements of the wear and those of the hair that are caused by flows and vibrations of air can enter the monitoring system as noises.

DISCLOSURE OF THE INVENTION

In view of the above-identified circumstances, it is therefore an object of the present invention to provide a biological information monitoring apparatus that can highly precisely observe a clothed subject who is taking any desired posture in order to make it conveniently utilizable and support the life of the subject.

A biological information monitoring apparatus according to the invention employs a high frequency electromagnetic wave (especially 300 GHz to 30 THz) including a terahertz band to remotely detect positional fluctuations of the surface of the skin of the subject so as to acquire biological information easily and conveniently. When such an electromagnetic wave is used, it is possible to acquire the temporal displacement of positional fluctuations, or the vibration component, by detecting the component of the electromagnetic wave transmitted through the wear and scattered and reflected by the surface of the skin of the subject.

If a short pulse electromagnetic wave with a pulse width of 3 psec is used as will be discussed in greater detail in the description of examples, it is possible to detect the amplitude of vibrations with a level of precision of the order of 100 μm by measuring the delay time of the electromagnetic wave. Therefore, it is possible to monitor a finely vibrating state that is produced by the pulse and/or the breathing of the subject. Such a short pulse can be generated, for instance, by means of a photoconductive element that is adapted to convert a short pulse laser beam irradiated onto it into an electromagnetic wave by applying a voltage to the electrodes formed on a GaAs substrate by low temperature growth and irradiating a short pulse laser beam. The reflected electromagnetic wave can also be detected by means of such an element. A remote sensing apparatus using an electromagnetic wave in the terahertz region can be realized as a small module by way of hybrid integration. The details of such an apparatus will become apparent from the description of examples.

If such a module is integrated into a wash basin, a chair or some other object that people use in daily lives, remaining there or in the vicinity thereof for a certain period of time per day, it is possible to acquire biological information including information on the pulse and the respiration of the subject without consciousness on the part of the subject. Additionally, the pulse rate, the pulse wave, the pulse propagation time, the blood pressure, the electrocardiographic wave and the degree of hardening of the arteries can be determined by waveform analyzing computations that are conducted on the basis of the acquired vibration-related information. Such data can be stored continuously in a memory section. Additionally, generalized patterns relating to such biological information that are stored in a database may also be stored in the memory section. Then, it is possible to judge the physical and emotional conditions of the subject by pattern matching. Information on such judgments can also be stored in the memory section so as to be displayed at a display section and/or notified to the user as voiced information. It can also be displayed at a terminal by way of a communication network and/or transmitted to a terminal by way of a mobile phone.

Information on such judgments can be output as behavior advices for maintaining the health of the subject and/or as assistance to the man-machine interface for the purpose of smoothly controlling the OA equipment, the navigation system, the robot and other machines and/or the electronic appliances that belong to the subject.

A biological information monitoring apparatus according to the invention can highly precisely observe a clothed subject who is taking any desired posture. Therefore, it can be utilized very conveniently to support the daily life of the subject. For example, it is possible to judge the physical and emotional conditions of the subject and give advices for the behavior of the subject by acquiring information on the pulse, the respiration and other activities of the body that cause vibrations of the body that are transmitted through the body and computing the pulse wave, the pulse rate, the blood pressure and so on. Additionally, it is possible to smoothly handle the interfaces of machines and electronic appliances that the subject operates.

BEST MODE FOR CARRYING OUT THE INVENTION

Embodiment 1

The first embodiment of biological information monitoring apparatus according to the invention is adapted to monitor biological information at the wash basin that the family members use several times a day in order to accumulate and provide information effective to maintain the health and support the daily lives of the family members without giving them any feeling of inconvenience.

Figure 1:
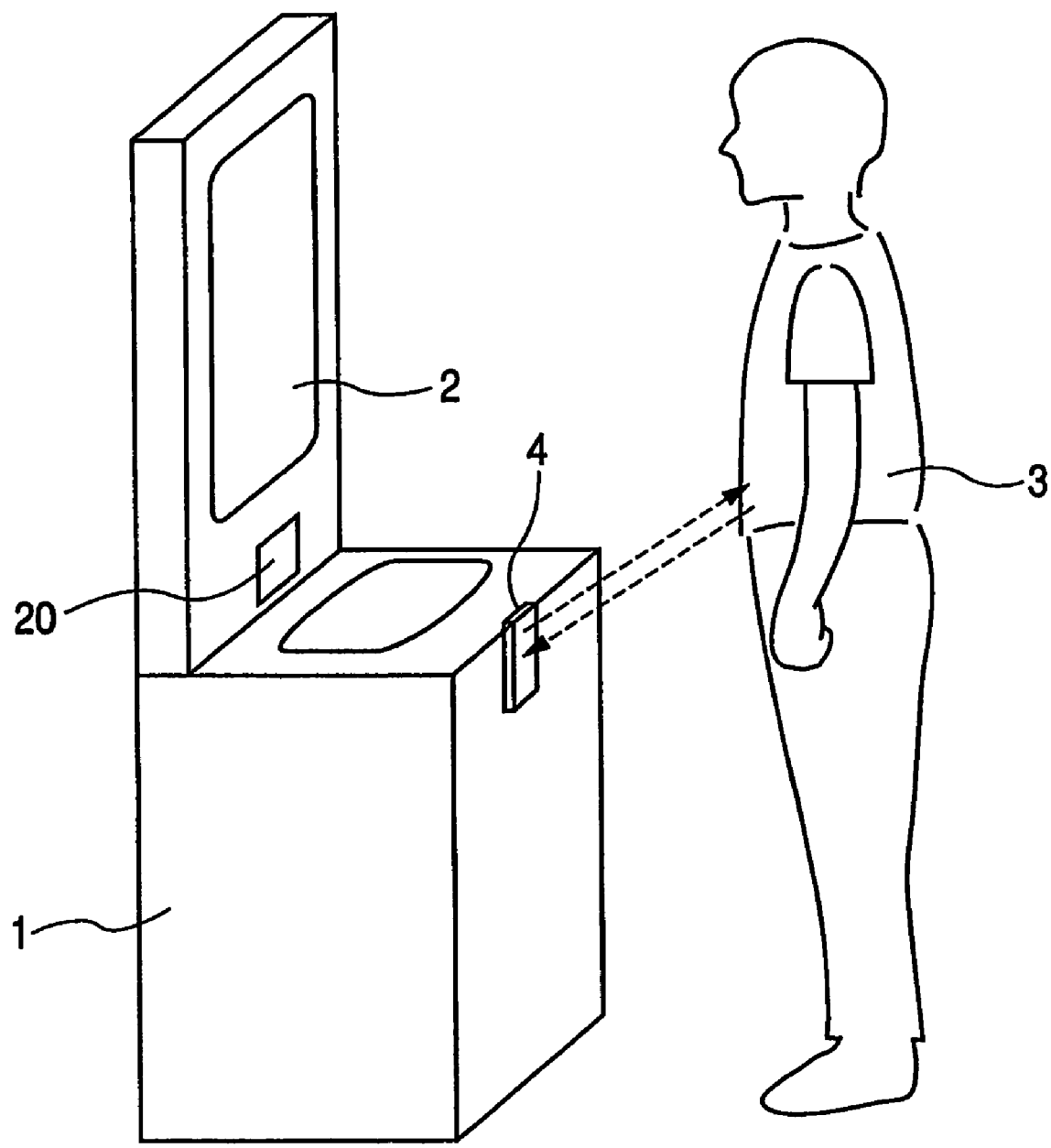
FIG. 1 is a schematic illustration of the first embodiment of biological information monitoring apparatus according to the invention.

FIG. 1 illustrates a situation where a person 3 is standing in front of a wash basin 1 that is provided with a mirror 2 and doing something. A remote sensing section 4 adapted to use an electromagnetic wave is buried in the wash basin in order to remotely acquire information on the person standing in front of the wash basin typically from the abdomen of the person. A technique of irradiating an electromagnetic wave having a wavelength longer than that of infrared rays and analyzing the reflected wave so as to analyze the vibrations of the body of the person from the acquired positional fluctuations may suitably be used for the purpose of remote sensing. The distance good for remote sensing is typically not longer than 1 m. A heat sensor 20 adapted to detect an approaching person may be arranged in the wash basin or the like for the purpose of turning on and off the switch of the monitoring apparatus. Instead of a heat sensor 20, a camera may be arranged to check if a person is standing in front of the wash basin or not and identify the person standing in front of the wash basin and the site of the body to be sensed by the bio monitor.

Figure 2A:
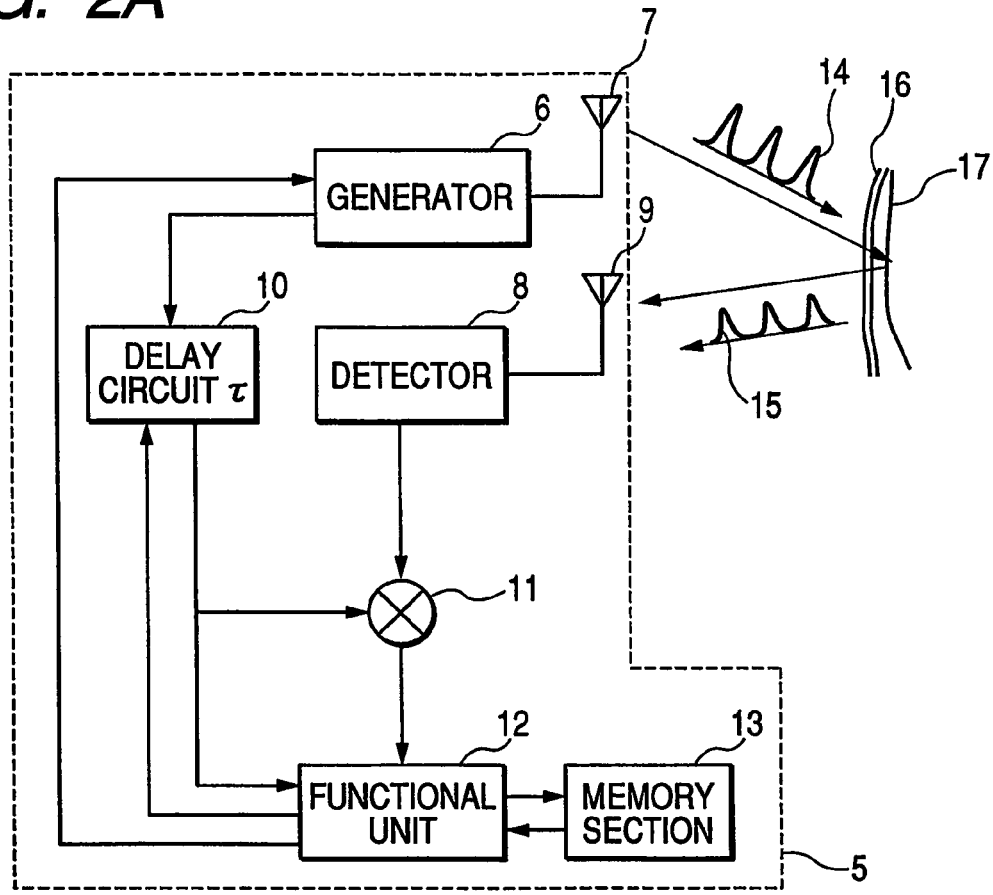
FIGS. 2A and 2B are schematic illustrations of a remote sensing apparatus according to the invention.

Now, a remote sensing operation using an electromagnetic wave will be described by referring to FIGS. 2A and 2B. Referring firstly to FIG. 2A illustrating a schematic block diagram of a sensing section of a biological information monitoring apparatus adapted to use an electromagnetic wave, numeral 5 generally denotes the sensing section. The electromagnetic wave 14 emitted from an antenna 7 is propagated through air toward a person and gets to the skin surface 17 of the abdomen of the person through the wear 16. The electromagnetic wave 14 is scattered as it gets to the skin surface and slightly penetrates into the inside of the skin and a part 15 of the scattered electromagnetic wave is transmitted through the wear 16 and arrives at antenna 9 as reception signal. A reflex type reflection sheet may preferably be applied to the site to be observed 17 of the body of the person in order to improve the sensitivity of the observation.

Figure 2B:
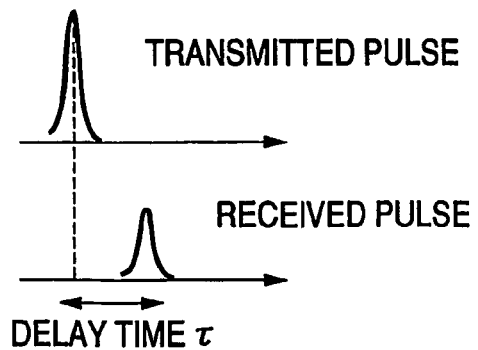

As shown in FIG. 2B, the positional fluctuations of the site to be observed 17 can be determined by detecting the change with time of the propagation delay time $\tau$ between the transmitted pulse and the received pulse of the electromagnetic wave. The sensing section 5 of the biological information monitoring apparatus comprises an electromagnetic pulse generator 6, an antenna 7 for emitting the generated electromagnetic pulse 14 into space, an antenna 9 and a detector 8 for receiving the reflection pulse 15 from a reflecting section 17, a delay circuit 10 for delaying the timing of pulse generation from that of the pulse generator 6, a mixer 11 for mixing the delayed transmitted pulse and the received pulse and a functional unit 12 for determining the distance between the reflecting section 17 and the sensing section 5 from the delay time $\tau$. If necessary, the sensing section 5 may additionally comprise a memory section 13 for storing the collected data. While the above listed components can be united in a cabinet or integrally prepared, it is not necessary to contain all of them in a cabinet. The output of the mixer 11 shows the largest output power when the timing of the delayed transmitted pulse and that of the received pulse agree with each other so that it is possible to detect the propagation delay tire of the electromagnetic wave and determine the distance between the reflecting section 17 and the sensing section 5 by sweeping and controlling the delay time of the delay circuit 10 by means of the functional unit 12. The output of the electromagnetic pulse from the pulse generator 6 may be made to fluctuate at a low frequency of the order of 1 kHz and a known synchronism detection technique may be used to take out the output of the mixer 11 as the mixing output obtained by using the low frequency signal. The cycle of generation of an electromagnetic pulse and the pulse position (phase) can also be controlled by the functional unit 12. If necessary, the multi-path effect is removed to improve the S/N ratio of the reception signal. More specifically, while it is difficult to separate noises due to reflections other than the reflection of the reflecting section 17 and echoes of the pulse that are produced as the pulse is reflected by walls if the cycle is fixed, they can be separated by changing the cycle according to a predetermined pattern and controlling the delay circuit 10 as a function of the change in the cycle. The predetermined pattern is stored in the memory section 13 and accessed for the purpose of computing the distance whenever necessary. If the electromagnetic wave is propagated through air at the light velocity c, the distance d can be determined by formula (1) below.

$$d = \tau c/2 \tag{1}$$

Now, the space resolution and the response speed of the remote sensing section for positional fluctuation analysis will be discussed. Firstly, the large positional fluctuations that occur slowly as a person moves are controlled by constantly resetting the delay time so that the minute fluctuations that occur as a result of an activity of the person can be isolated. At the same time the influence of the electromagnetic delay due to the wear is also calibrated. A known wobbling technique of modulating the delay time with a very small amplitude for synchronous detection may be employed as a technique for locking the movement of the body of the subject for the purpose of resetting the delay time.

The vibrations due to the pulse and the respiration to be remotely sensed are reflected to the overall movement of the person along with the vibrations of the surface of the abdomen. The vibration frequency of the pulse is about 3 Hz and that of the respiration is about 0.5 Hz at most and it is only necessary to detect an amplitude of not greater than 1 mm. Signal separation is possible because, additionally, the speed at which a person moves while using the wash basin is slower or not cyclic but the amplitude of the movement is large.

In practice, it is desirable for the sensing section to be sensitive to a band ten times as wide as the vibration frequency to be detected so that it is designed to operate at 30 Hz or a sampling rate of about 30 msec. If the amplitude of the vibrations to be detected is 1 mm, the delay time that corresponds to the difference of distance is about 6.7 psec as determined by using the formula (1). Therefore, it may be sufficient to be able to sweep a delay of 13 psec, which is about twice as long as the delay time, at every 30 msec. Of course, the cycle of synchronous detection and that of transmission of an electromagnetic pulse have to be higher than that and need to be about 1 kHz. Here, 1 kHz is employed for the cycle of the synchronous detection, and 76 MHz is employed for the frequency of the electromagnetic pulse. The resolution of the vibration amplitude is mainly defined by the pulse width of the electromagnetic pulse. From the formula (1), while a level of precision of delay time of 6.7 psec is required for the precision of 1 mm, the use of a pulse with a half width of about 33 psec will be satisfactory if signal separation of about ⅓ of the pulse half width is possible. Differently stated, a positional fluctuation analysis can be successfully conducted to an amplitude of about 100 μm for a pulse of about 3 psec.

An oscillation circuit using a high-speed electronic device typically having a high-electron-mobility transistor ("HEMT") structure is used to generate such a short pulse. Instead of the circuit for generating a short pulse of this embodiment, a circuit for generating and detecting a continuous high frequency sinusoidal wave such as a millimeter wave or a terahertz wave may alternatively be used. The electromagnetic wave generating section is realized preferably in the form or a highly directional antenna or provided with a lens in order to effectively irradiate a beam to the site to be observed and accurately control the direction of propagation.

Figure 3:
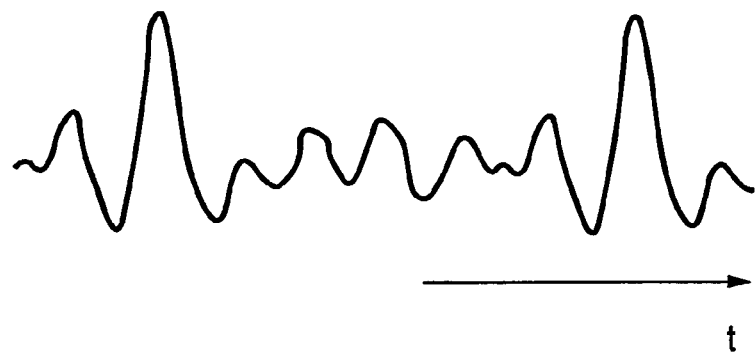
FIG. 3 is a schematic illustration of monitoring waveforms of a remote sensing apparatus according to the invention.
Figure 4:
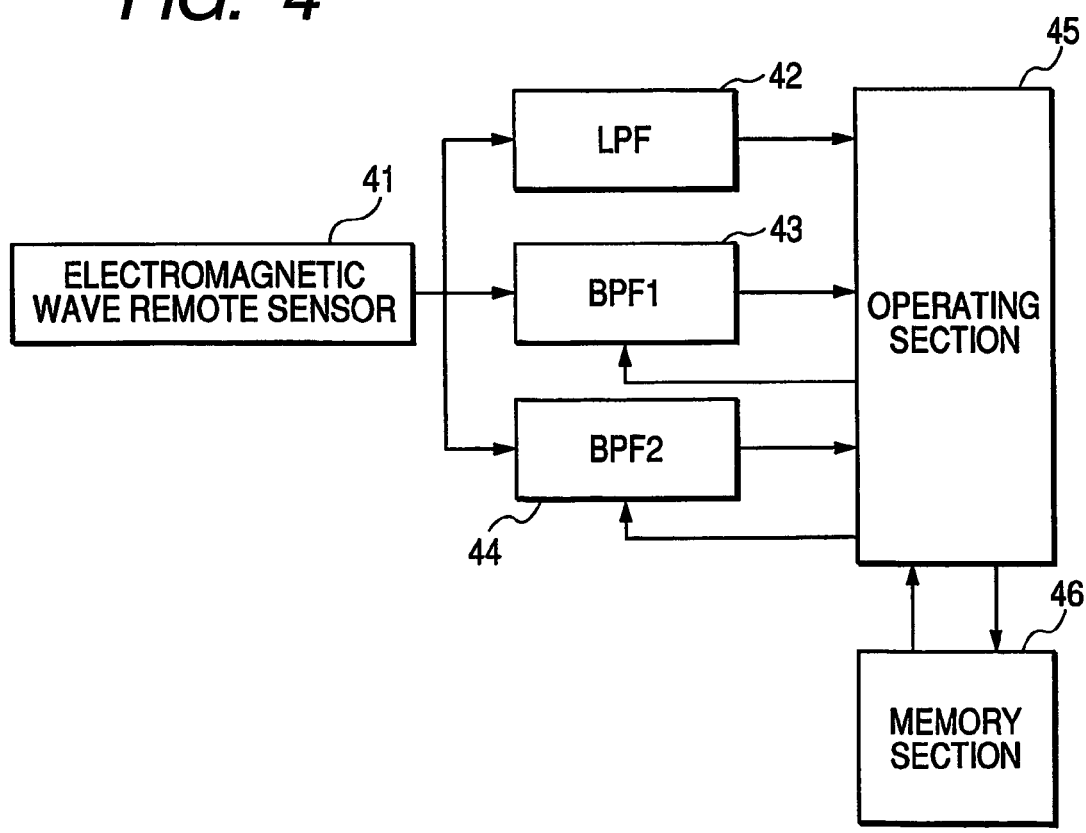
FIG. 4 is a schematic block diagram of a biological information analysis system according to the invention.

FIG. 3 schematically illustrates a detected vibration waveform. It is possible to detect a waveform that corresponds to the vibrations generated by the pulse of the body. The vibrations caused by respiration will be detected as fluctuations of an envelop (not shown) that take place with a slower cycle. FIG. 4 shows a schematic block diagram of a signal analysis system that can be used for the embodiment. The output from the functional unit of the remote sensor 41 that is transmitted by means of an electromagnetic wave as described above by referring to FIGS. 2A and 2B is subjected to signal separation by means of a plurality of filter circuits 42 through 44 and then to vibration analysis at operating section (processing section) 45 and extracted as bio-monitor signal. The memory section 46 stores accumulated bio-signal patterns as database, which are utilized by the operating section 45 for pattern matching. The database may include both the data obtained from the functions of ordinary human bodies and the data of specific individuals accumulated by the apparatus of the embodiment. The output of the operating section 45 can be taken out whenever necessary as information on each of the specific individuals for any of different time zones. Thus, advices for the behavior of a person in a particular time zone of today may be output after taking in the data on the physical and emotional conditions of the person. The advices may be directly output audibly and/or visibly by way of a speaker and/or a display buried in the wash basin and/or transmitted to a personal computer and/or a mobile phone by data transmission. The operating section, a data output means and a data transmission means for transmitting data to a network may be contained in the wash basin. The mirror 2 may be provided with a display feature.

While three filters are arranged in FIG. 4, the number of filters is not limited to three. In FIG. 4, low-pass filter (LPF) 42 is designed to extract fluctuations generated as a result of movements of the subject that are not related to biological information. The signal from the low-pass filter is used as correction signal when extracting biological information. Band-pass filter 1 (BPF1) is designed to take out the signal of the pulse of the subject. It may be a variable band-bass filter provided with a feedback control feature of feeding back the outcome of the operation of the operating section so as to select an optimum band depending on the circumstances. Band-pass filter 2 (BPF2) is designed to take out the signal of the respiration of the subject. Likewise, it may be a variable band-pass filter adapted to select an optimum band depending on the circumstances. Since the pulse and the respiration of a subject is correlated, the feedback control operation of the filters may be such that the band selections proceed to intensify the correlation. A technique using an FFT, a technique using a local oscillator for heterodyne detection or a combination thereof may be used for waveform analysis.

With the above-described method, it is possible to acquire a plurality of pieces of biological information by means of a single remote sensing apparatus. As for the pulse, various pieces of information can be obtained and judged on the subject by analyzing not only the pulse rate but also the waveform of the pulse wave. Such pieces of information include information on the electrocardiographic wave, the blood pressure and the degree of hardening of the arteries. It is possible to estimate the emotional condition (joy and anger) of the subject by analyzing the state of the sympathetic nerve and that of the parasympathetic nerve on the basis of the acquired information on the pulse wave, the blood pressure, the respiration and so on to thereby output the emotional condition by the operation section. It is possible to determine the above-described advices for the behavior of the person by taking the emotional condition into consideration.

Thus, as the wash basin is equipped with a sensor for remotely acquiring information on the vibrations of the skin surface of the person and an operating section, the biological information monitoring apparatus can support the behavior of the person. The information acquired as a result of monitoring is accumulated in the operating section. The advices or the like may be output on site or a system may be built to provide the advices by way of a network. A biological information monitoring apparatus according to the invention may be installed in a kitchen, a toilet, a television set or a office table where a person stays for a certain period of time instead of a wash basin.

Embodiment 2

The second embodiment of the present invention is a small module of a remote sensing apparatus as described above for the first embodiment. A number of such modules may be arranged at different sites in order to simultaneously acquire biological information from a person. This arrangement is effective for accurately acquiring and correcting information on vibrations and the state of propagation of vibration in the body of the person.

Figure 5:
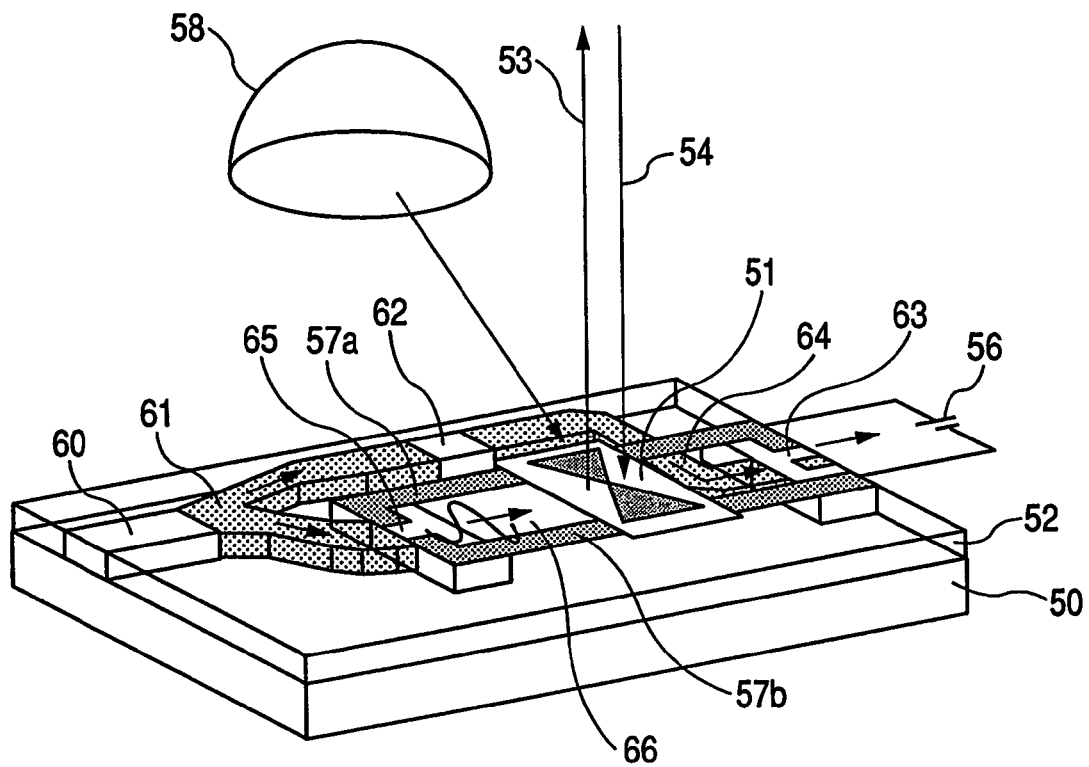
FIG. 5 is a schematic illustration of an integrated module that can be used for a remote sensing apparatus according to the invention, showing the structure thereof.

FIG. 5 schematically illustrates an integrated module according to the invention. A semiconductor mode-locked laser 60 is mounted on a substrate 50 and adapted to generate a pulse of about 0.3 psec that is coupled to an optical waveguide 61. One of the propagated laser beams branched by the optical waveguide 61 is irradiated onto a terahertz wave generator 65 and converted into an electromagnetic wave 66 having a pulse width of about 0.5 psec, which is then propagated through transmission paths 57a, 57b. The other laser beam is propagated by way of an optical delay circuit 62 and an optical path 64 and irradiated onto a photo-detector 63.

The configuration of the module will be described below. Photosensitive insulating resin 52 is formed on a half-insulating GaAs substrate 50 and the Y-branching optical waveguide 61 is formed in part of the resin 52 by means of photolithography so as to show a refractive index higher than that of the surrounding area. Photosensitive polysilane [Gla-sia: tradename, available from Nippon Paint Co., Ltd.] may suitably be used for the resin. Other resin materials that can suitably be used for the optical waveguide/electric insulating layer include BCB, polyimide and other optical resin materials that are photosensitive. The terahertz wave generator 65 is a photoconductive switching element prepared by forming electrodes on a substrate of undoped LT-GaAs that is formed by means of a low temperature growth technique.

As a voltage is applied between the electrodes 57a, 57b that operate also as transmission paths and a laser pulse beam is irradiated onto the generator 65 with a wavelength of about 800 nm, an electromagnetic pulse is generated from the generator 65.

The photo-detector 63 is also an photoconductive switching element having a structure similar to that of the terahertz wave generator. It is adapted to generate photo carriers only at a timing of irradiation of a laser pulse beam so that an electric current flows as a function of the magnitude of the electric field of the electromagnetic pulse propagated through the transmission paths. The electric current can be detected as signal. Thus, it is possible to observe the change with time of the intensity in the electric field of the terahertz pulse by changing the delay time of the delay circuit 62. The delay circuit 62 may be designed as a delay waveguide, an optical switch or an element adapted to change its refractive index (not shown). The technique that is used for detecting a terahertz pulse in the embodiment may be replaced by a technique of arranging an electro-optic ("EO") crystal upstream relative to the photo-detector so as to transform the change with time of the intensity of the terahertz pulse into the Pockels effect of the EO crystal and observe the intensity of the transmitted beam branched from the pulse laser by means of the photo-detector.

Then, it is possible to examine the vibrations of the surface of the skin of a person without contacting the skin by emitting an electromagnetic wave 53 into space by means of antenna 51, observing the reflected electromagnetic wave 54 that is scattered by the person and examining the positional fluctuations of the reflecting body as in the case of the first embodiment. A module for generating an electromagnetic wave and a module for detecting the reflected electromagnetic wave may be arranged side by side to observe the reflected electromagnetic wave. A semispherical lens 58 may be arranged on the antenna to control the beam and irradiate it with a low radiation angle. Alternatively, a movable antenna may be used to make the direction of beam propagation swing.

Figure 6:
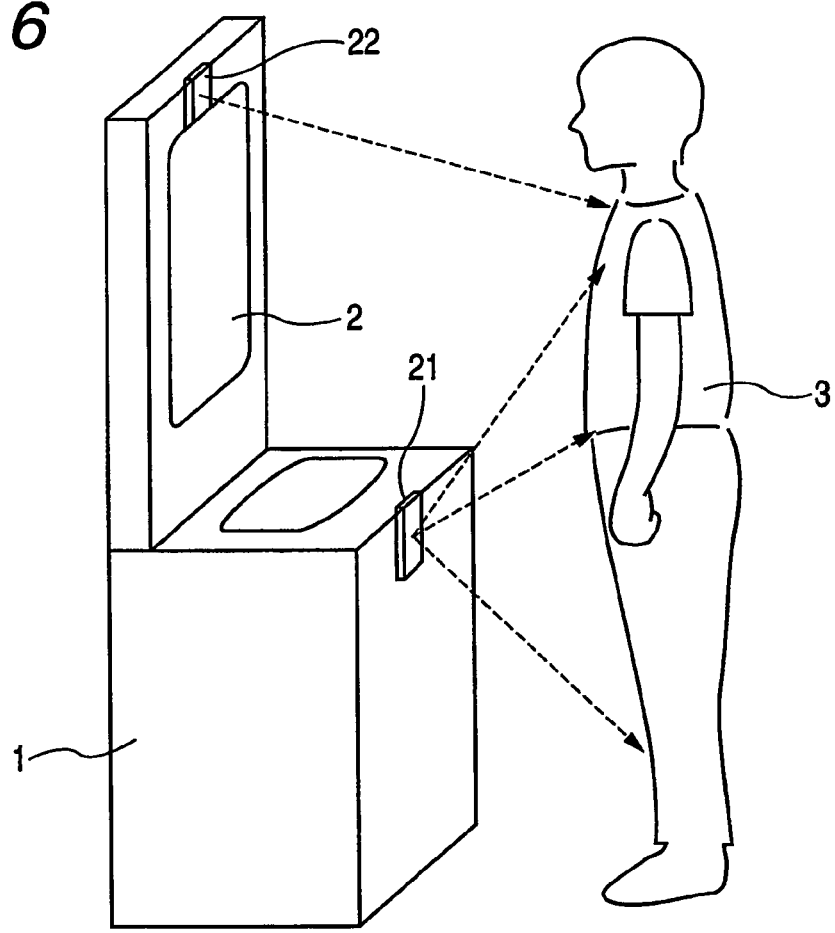
FIG. 6 is a schematic illustration of the second embodiment of biological information monitoring apparatus according to the invention.

It is possible to acquire biological information simultaneously from a plurality of sites of the body of the subject by burying so many sensing modules like the sensing modules 21, 22 in the wash basin, as the first embodiment, and scanning the body. Note that, in FIG. 6, the components same as those of FIG. 1 are denoted respectively by the same reference symbols. It is possible to grasp the propagation of the pulse wave in the body by observing the pulse wave at a plurality of sites. The accuracy of the evaluation of the blood pressure, the degree of hardening of the arteries, the degree of mental relaxation and so on can be improved when the speed of propagation of the pulse wave is determined. Personal information including the age, the body weight, the height and so on may be input to the remote sensing system and/or scales provided with electrodes may be buried in the floor to take in information on the body weight, the body fat, the perspiration and so on of the subject in order to improve the accuracy of judgment of the remote sensing system.

Figure 7:
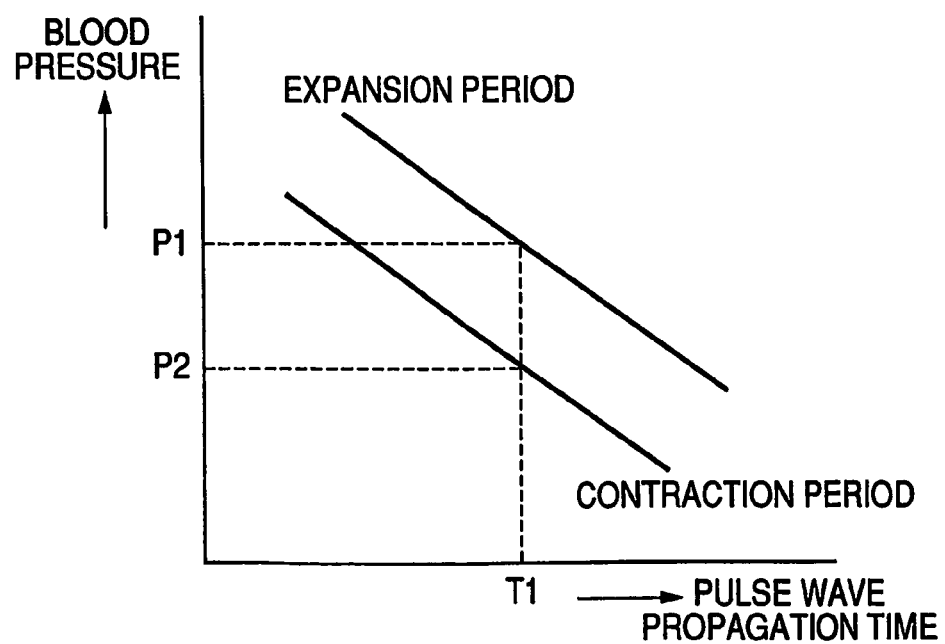
FIG. 7 is a schematic illustration of a blood pressure monitoring method.

FIG. 7 is a graph illustrating the relationship between the pulse wave propagation time and the blood pressure. Information on the vibrations of the skin surface is acquired from a plurality of sites including the chest, the abdomen and the feet. As the pulse wave propagation time is determined, it is possible to by turn determine the highest blood pressure P1 and the lowest blood pressure P2 by referring to the judgment line for the expansion period and the judgment line for the contraction period. The judgment lines can be defined on the basis of the initial personal information including the age, the body weight and the height of the subject and the stored relationship between the blood pressure and the pulse wave propagation time. When automatically judging the physical and emotional conditions of the subject by referring to the stored data, it is preferable to identify the person standing in front of the wash basin. Any of the known techniques for recognizing the finger print, the iris, the face or the like may be used for the purpose of personal identification.

Thus, this embodiment is adapted to remotely acquire vibration-related information of the subject by remote sensing, using small modules so that it is possible to acquire biological information simultaneously from a plurality of sites of the body of the subject where so many modules are buried and hence improve the accuracy of judgment.

Embodiment 3

Figure 8:
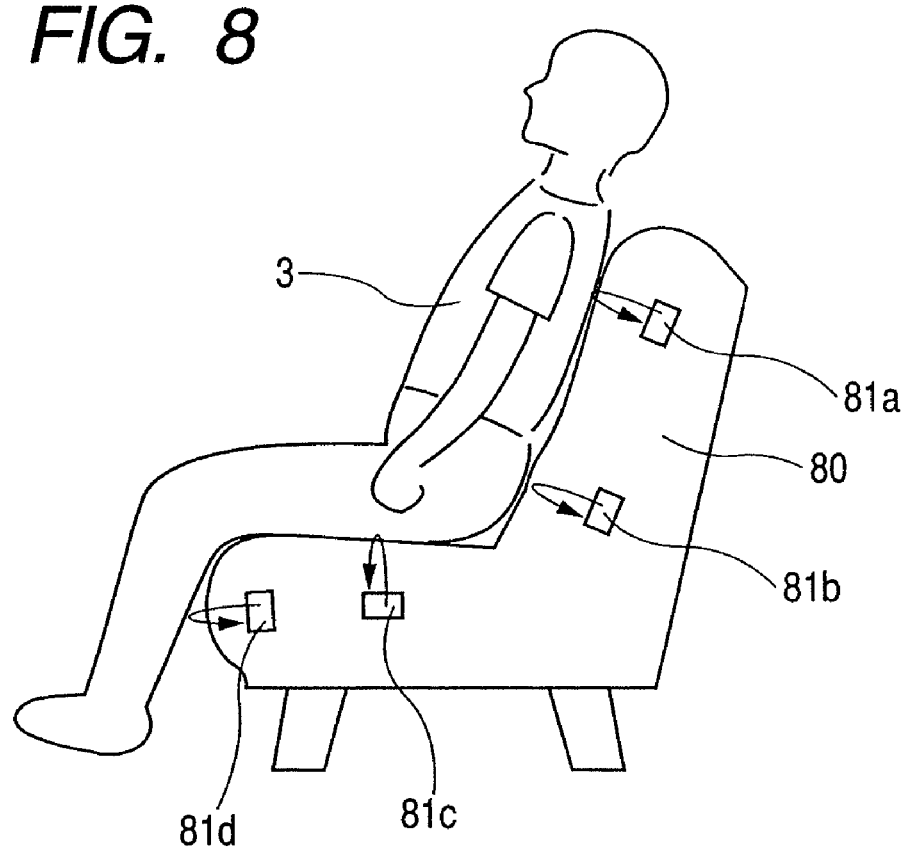
FIG. 8 is a schematic illustration of the third embodiment of biological information monitoring apparatus according to the invention.
Figure 9:
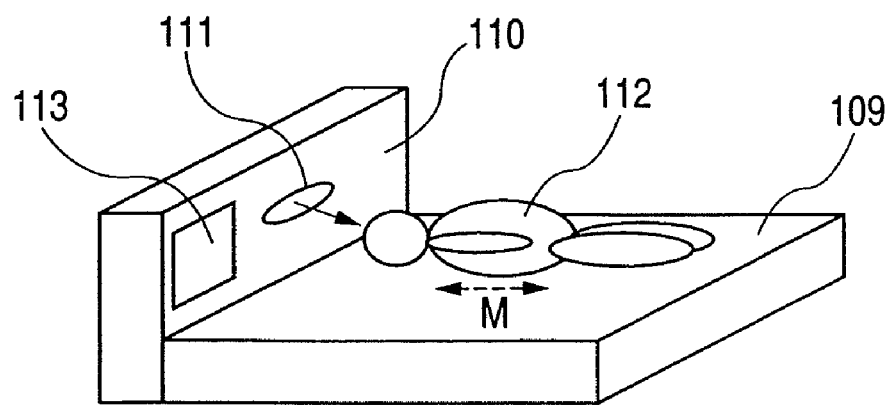
FIG. 9 is a schematic illustration of a known biological information monitoring apparatus.

The third embodiment of the present invention is adapted to bury sensors 81a through 81d of the above described type in a chair 80 as shown in FIG. 8. Note that, in FIG. 8, the components same as or similar to those of FIG. 1 are denoted respectively by the same reference symbols.

Known vibration sensors are adapted to be arranged on or near the surface of a chair and hence are accompanied by problems particularly in terms of the appearance, the design and the comfortableness of the chair. To the contrary, electromagnetic type modular sensors according to the invention can be contained in a chair to allow a high degree of design freedom comparable to that of ordinary chairs without damaging the comfortableness of the chair.

Additionally, unlike known sensors, the subject is not required to hold the back in tight contact with the back cushion of the chair and sit still. This is because the electromagnetic wave of millimeter to terahertz range to be used for observation is propagated through air and transmitted through the back cushion and the cloth of the chair and the wear of the subject.

With this embodiment again, a plurality of sensors can be arranged at so many sites to acquire so many pieces of biological information simultaneously.

Activities of persons sitting on a chair include jobs relating to office activity equipment in offices, attendance to meetings, car driving, watching pictures and listening to music at home. Therefore, an apparatus according to the invention can be used as assistance to the man-machine interface for such an activity in addition to the grasping the physical and emotional conditions of the subject and providing advice for the behavior of the subject.

For example, the degree of relaxation of the subject can be evaluated by analyzing both the signal on the fluctuations of the pulse rate and the signal on the respiration of the subject. Therefore, when the apparatus produces a menu to receive a command from the subject, it is possible to select a menu that matches the taste of the subject or optimally guide the activity of the subject by judging the emotional condition of the subject. In other words, an apparatus according to the invention can operate as interface. Additionally, an apparatus according to the invention can learn the direction in which it should guide the subject so as to improve its ability of producing a menu that optimally matches the taste of the subject.

In the case of pictures and music, an apparatus according to the invention can be adapted not to produce a wide choice of subjects over a large number of genres but to select a title that optimally matches personal conditions of the subject. In the case of office works, an apparatus according to the invention can be adapted to rearrange the files, the software or the working schedule that the responsible PC presents and provide advices to the use of OA equipment, the theme of a meeting and redirecting a meeting and so on. An apparatus according to the invention can also find applications in the field of comprehensive car navigation systems that are adapted to take the traffic jams in the related roads and the degree of safety of the roads into consideration.

In any case, according to the invention, it is possible to provide a system for assisting the daily lives of people that can automatically acquire biological information from the people without giving any unpleasant feeling to and being recognized by the people.

While the present invention is described mainly in terms of a system comprising sensors that are adapted to be buried and used without being noticed by people, such sensors can be incorporated into a robot that is required to cooperate with people so as to operate as remote sensing and feedback means so that people can be positively assisted by the robot on the basis the biological information of the people acquired by the system.

While the present invention is described above in terms of human being, it can find applications in living things having a pulse system and a respiration system.

This application claims priority from Japanese Patent Application No. 2004-092401 filed on Mar. 26, 2004, which is hereby incorporated by reference herein.

The invention claimed is:

1. A biological information monitoring apparatus for monitoring biological information by acquiring information on positional displacements of a surface of a living body, said apparatus comprising:
   an electromagnetic wave generating unit for generating an electromagnetic wave of a frequency band between 300 GHz and 30 THz and radiating it into air;
   an electromagnetic wave detecting unit for detecting the electromagnetic wave scattered by the surface of the living body;
   a first computational-determination unit for computationally determining changes with time of the positional displacements of the surface of the living body from a state of propagation of the electromagnetic wave;
   a second computational-determination unit for computationally determining characteristic quantities of the living body from the changes with time as biological information; and
   a memory unit for storing characteristic quantities of a living body in advance,
   wherein an output signal obtained as biological information from said second computational-determination unit is compared with the characteristic quantities stored in said memory unit to judge physical conditions relating to a blood pressure or a degree of hardening of arteries of the living body, and a result of judgment is displayed by characters or output by voice sounds.

2. The apparatus according to claim 1, the electromagnetic wave is a short pulse that is generated repeatedly and the half-width of the pulse is not greater than 33 psec.

3. The apparatus according to claim 1, wherein the changes with time of the positional displacements of the living body at a plurality of sites are computed by said computational-determination unit by the electromagnetic wave and the state of propagation of the characteristic quantities as computed from the changes with time can be detected.

4. The apparatus according to claim 1, wherein said biological information monitoring apparatus is contained in a wash basin, a toilet, or a chair, and biological information is remotely acquired by said apparatus.

5. A biological information monitoring apparatus for monitoring biological information by acquiring information on positional displacements of a surface of a living body, said apparatus comprising:
   an electromagnetic wave generating unit for generating an electromagnetic wave of a frequency band between 300 GHz and 30 THz and radiating it into air;
   an electromagnetic wave detecting unit for detecting the electromagnetic wave scattered by the surface of the living body;
   a first computational-determination unit for computationally determining changes with time of the positional displacements of the surface of the living body from a state of propagation of the electromagnetic wave;
   a second computational-determination unit for computationally determining characteristic quantities of the living body from the changes with time as biological information; and
   a memory unit for storing characteristic quantities of a living body in advance,
   wherein an output signal obtained as biological information from said second computational-determination unit is compared with the characteristic quantities stored in said memory unit to judge emotional conditions referring to a degree of relaxation, a degree of stress or a state of joy or anger of the living body, and a result of judgment is fed back to a machine or an electronic appliance and utilized as control signal for interface for operating the machine or the electronic appliance.

6. A biological information monitoring apparatus for monitoring biological information by acquiring information on positional displacements of a surface of a living body, said apparatus comprising:
   an electromagnetic wave generating unit for generating an electromagnetic wave of a frequency band between 300 GHz and 30 THz and radiating it into air;

an electromagnetic wave detecting unit for detecting the electromagnetic wave scattered by the surface of the living body;

a first computational-determination unit for computationally determining changes with time of the positional displacements of the surface of the living body from a state of propagation of the electromagnetic wave;

a second computational-determination unit for computationally determining characteristic quantities of the living body from the changes with time as biological information; and a memory unit for storing characteristic quantities of a living body in advance, wherein an output signal obtained as biological information from said second computational-determination unit is compared with the characteristic quantities stored in said memory unit to judge physical and mental conditions of the living body, and a result of judgment is fed back to a machine or an electronic appliance and utilized as control signal for interface for operating the machine or the electronic appliance.

\* \* \* \* \*